United States Patent [19]

Ankartross et al.

[11] Patent Number: 4,750,483

[45] Date of Patent: Jun. 14, 1988

[54] DEVICE FOR GASIFICATION AND DOSAGE

[75] Inventors: Jan O. Ankartross, Vallentuna; Ulf G. Lundell, Grodinge; Rune Nyman, Solna, all of Sweden

[73] Assignee: Gambro Engstrom AB, Sweden

[21] Appl. No.: 3,720

[22] Filed: Jan. 16, 1987

[30] Foreign Application Priority Data

Jan. 21, 1986 [SE] Sweden .............................. 8600250

[51] Int. Cl.$^4$ ...................... A61M 15/00; A61M 16/00
[52] U.S. Cl. ............................... 128/203.26; 261/130; 128/200.11; 128/203.25; 128/203.13
[58] Field of Search .................. 128/202.22, 203.25, 128/203.27, 200.11, 201.13, 203.12, 203.13, 203.16, 203.16; 261/130

[56] References Cited

U.S. PATENT DOCUMENTS 4,038,980 8/1977 Fodor .............................. 128/203.27
4,538,604 9/1985 Usry et al. ...................... 128/204.25

Primary Examiner—William E. Kamm
Assistant Examiner—George Manuel
Attorney, Agent, or Firm—Lerner, David, Littenberg, Krumholz & Mentlik

[57] ABSTRACT

Apparatus for delivery predetermined dosages of anesthetic gases are disclosed, including a reservoir for supply of anesthetic liquid, gasification chamber, a riser for delivering anesthetic liquid from the reservoir to the gasification chamber which is maintained at a predetermined temperature at which the anesthetic liquid is converted directly into anesthetic gas, a gas supply for maintaining the anesthetic liquid under a predetermined gas pressure which substantially corresponds to the pressure at which the anesthetic liquid is delivered to the gasification chamber, and a delivery line for controllably delivery the anesthetic gas from the gasification chamber.

11 Claims, 1 Drawing Sheet

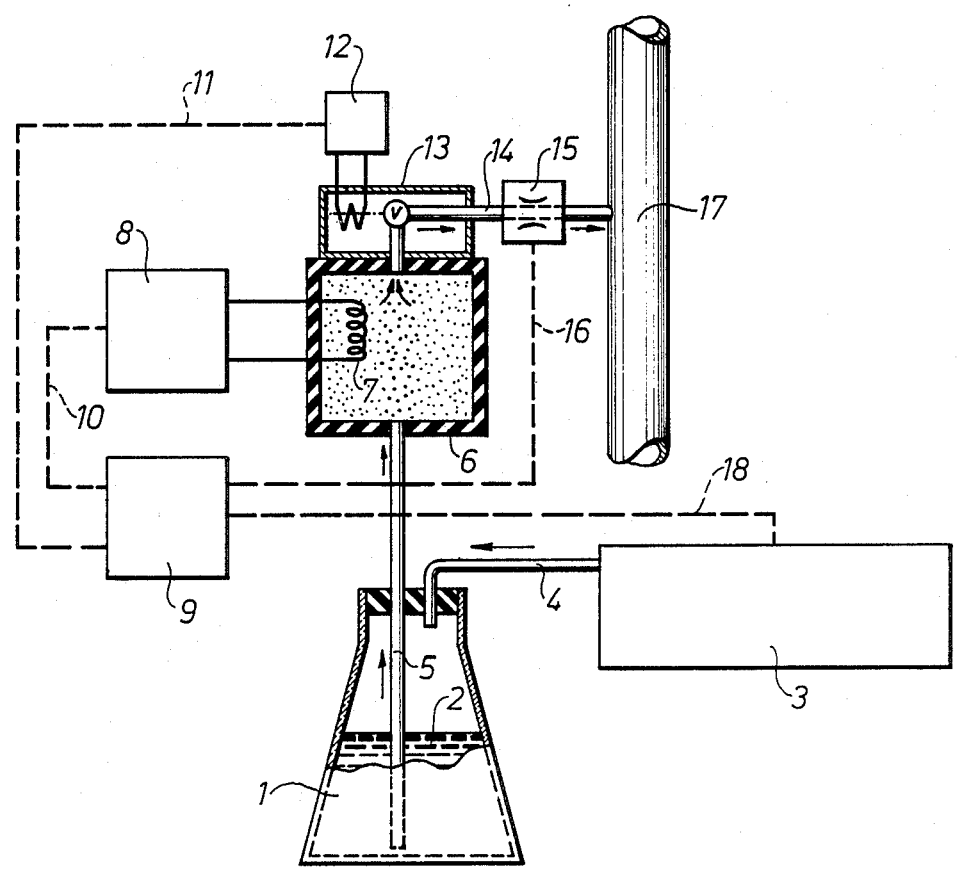

DEVICE FOR GASIFICATION AND DOSAGE

FIELD OF THE INVENTION

The present invention relates to apparatus for the gasification and dosage of various materials. More particularly, the present invention relates to such apparatus for feeding an anesthetic gas to a fresh gas stream in an anethesia apparatus. More particularly, the present invention relates to such apparatus including a source of liquid which is intended for gasification, a gasification chamber, and a dosage line for conducting the gas from the gasification chamber to a mixing point for admixture with another gas, such as a fresh gas stream. It will be apparent to those versed in this art, however, that the apparatus of the present invention can also be used for other purposes, such as for the moistening of breathing gases in respiration apparatus and the like.

BACKGROUND OF THE INVENTION

Various techniques have been utilized in the past in an attempt to gasify anesthetic liquids or moistening liquids to be applied directly into fresh gas streams. For example, U.S. Pat. Nos. 3,251,361 and 4,038,980, as well as Swedish Patent Application Ser. No. 84.03447-9, disclose various such systems. In these systems, however, it has proven difficult to provide uniform and controllable dosages from such systems. In U.S. Pat. No. 4,038,980, for example, an air humidifier 2 is employed in which water is fed from a reservoir 50 through insert 32 for evaporation upon contact with a heated sheath 22, which is maintained at a temperature of between about 200° to 300° C. The humidifier itself is contained within an inspiraton line, which cannot be said to be maintained at a constant pressure. Other attempts have been made to effectuate the gasification of anesthetic liquids in separate gasification chambers where both gas and liquid phases exist simultaneously. In connection with these attempts, however, problems have arisen in connection with refilling these chambers with fresh liquid. In accordance with the present invention, however, these and other problems have now been solved in a surprisingly simple manner.

SUMMARY OF THE INVENTION

In accordance with the present invention, it has now been discovered that these and other objectives can now be accomplished by providing apparatus for delivering predetermined dosages of anesthetic gases to a primary gas supply which includes reservoir means for maintaining a supply of the anesthetic liquid, gasification means comprising a gasification chamber, delivery means for delivering the liquid anesthetic from the reservoir means to the gasification chamber, temperature control means for maintaining the gasification chamber at a predetermined temperature at which the anesthetic liquid is converted directly into anesthetic gas, pressure control means for maintaining the pressure of the anesthetic gas within the gasification chamber substantially constant, and delivery line means for controllably delivering the anesthetic gas from the gasification chamber to the primary gas supply at that substantially constant pressure.

In accordance with one embodiment of the apparatus of the present invention, the pressure control means includes liquid pressure control means for maintaining the pressure at which the anesthetic liquid is delivered to the gasification chamber substantially constant. In a preferred embodiment, the liquid pressure control means includes gas supply means for maintaining the anesthetic liquid under a predetermined gas pressure which substantially corresponds to the pressure at which the anesthetic liquid is delivered to the gasification chamber.

In accordance with another embodiment of the apparatus of the present invention, the delivery line means includes control valve means for opening and closing the delivery line means whereby the frequency and period of the opening and closing of the control valve means can be controlled thereby.

In accordance with another embodiment of the apparatus of the present invention, the delivery line means include a throttle valve, and throttle valve control means are preferably provided for controlling the throttle valve.

In accordance with another embodiment of the apparatus of the present invention, the gasification chamber is located above the reservoir means, and the delivery means includes riser means extending into the reservoir means to a point below the level of anesthetic liquid therein. In a preferred embodiment, the gasification chamber includes a bottom wall portion and the riser means extends to the bottom wall portion of the gasification chamber. In a more preferred embodiment, the gasification chamber also includes a top wall portion, and a delivery line means extends from the top wall portion of the gasification chamber.

In accordance with another embodiment of the apparatus of the present invention, condensation means are also included for converting the anesthetic gas back to its liquid state.

The present invention thus provides apparatus in which the gasification chamber is adapted to be maintained at constant pressure and at a predetermined temperature which is such that the liquid fed into the gasification chamber is directly gasified therein. In this manner, after equilibrium has been reached, a uniform amount of gas, at constant pressure and temperature, is obtained from which smaller quantities can readily be apportioned into another gas, such as a fresh gas, in an anesthesia apparatus. This constant pressure is preferably obtained by feeding the liquid which is to be gasified at that pressure, and this in turn can be achieved by maintaining the source of liquid at this pressure by feeding a separate gas supply' such as air, under that same pressure from a source of pressure through a governor.

In order to achieve the required dosages, the dosage line may be provided with a time-controlled valve, so that the opening frequency and/or opening time thereof can be varied. Alternately, the dosage line can be provided with a throttle valve, which is preferably controllable. The present invention can also be applied to liquid dosages in which a condensation stage is employed directly after the aforementioned dosage valve, and the dosage thus takes place in a gaseous state whereopon the gas is then reformed into a liquid state. In this manner, very precise methods for dosages, especially of small quantities of liquid, can be achieved.

BRIEF DESCRIPTION OF THE DRAWINGS

The present invention can be more fully understood with reference to the following detailed description, and to the attached drawing, which shows a side, partially sectional, schematic representation of the apparatus of the present invention.

DETAILED DESCRIPTION

Referring to the drawing, a preferred embodiment of the apparatus of the present invention is shown which is intended for use in anesthesia apparatus. The following discussion will thus relate directly to such an application, although it will be clear to those skilled in this art that the same principle can also be applied for other purposes.

In the drawing a source or reservoir 1 for an anesthetic liquid 2 is shown. This reservoir may comprise a liquid-filled pressure-proof glass flask which is intended to be supplied with a constant pressure. A source of pressure, which includes a pressure control governor, is provided for maintaining this constant pressure, there elements being jointly designated by reference numeral 3. This may be accomplished by simply feeding compresed air into the reservoir 1 through line 4. The liquid 2 is thus made to rise within riser pipe 5 up to a gasification chamber 6, which by means of a heating arrangement 7, which is shown schematically in the drawing, is adapted to be maintained at a predetermined temperature such that substantially all of the liquid fed into the chamber 6 is directly gasified. This heating can be controlled by means of a temperature control device 8, which in turn may be controlled by a microprocessor or the like 9. This control function is indicated by broken line 10. Broken line 11 indicates how this same microprocessor 9 can also control an electronic control device 12 for a solenoid valve 13 which is also shown schematically, and which controls the flow in a dosage line 14. Dosage line 14 may contain a flow control throttle valve 15, which may also be controllable by microprocessor 9, as indicated by broken line 16. Dosage line 14 terminates in a fresh gas line 17, only a small section of which is shown in the drawing. Reference numeral 18 is meant to indicate that the microprocessor 9 may also be adapted to control the combination of governor and source of pressure designated by reference numeral 3.

In the case of such commonly occurring anesthetics as halothane, n-furan or isofuran, it has proven to be appropriate to make use of a temperature of about 70° to 80° C. in gasification chamber 6. At the same time, it has proven appropriate to utilize pressures on the order of magnitude of about a 400 cm water column, that is to say about 0.4 bar. Thus, the pressure in gasification chamber 6 may not rise above about a 400 cm water column, since in that case the liquid would be pressed back toward the reservoir 1. Within the aforementioned temperature range the liquid gasifies directly as it enters the gasification chamber 6. At the same time, no more liquid can be introduced into the chamber 6 than that amount which has been apportioned through dosage line 4.

In a practical embodiment, a constant opening duration of the solenoid 12 of about 60 ms. is used, with the opening frequency being varied between about 0.1 and 10 Hz. At the same time, a throttle 15 can be used which is set up so as to provide a dosage of about 1 ml. per stroke. As a result, the dosage can be readily varied between about 0.1 and 10 ml/s. Alternatively, it is also possible to vary the duration of each such opening. By using a solenoid valve this would be possible from a minimum time of about 20 ms. up to being kept open permanently.

The pressure may of course also be varied, but this will be limited in practice by the strength of the flasks from which the anesthetic gas is normally supplied in liquid form. The lower pressure limit will be controlled by the fact that if the pressure were too low the liquid level in the vessel 1 would become decisively important in determining the dosage. In practice a pressure between about a 100 and 800 cm water column is preferably used.

Although the invention herein has been described with reference to particular embodiment, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, this invention may also be applied to the dosage of liquid. In such applications, the device 15 shown schematically may constitute a condensation apparatus in which the quantity of liquid metered in gaseous state is converted back into its liquid form.

What is claimed is:

1. Apparatus for producing predetermined dosages of an anesthetic gas comprising reservoir means for maintaining a supply of anesthetic in liquid form, gasification means comprising a gasification chamber, first delivery means for delivering said anesthetic in liquid form from said reservoir means to said gasification chamber, temperature control means for maintaining said gasification chamber at a predetermined temperature at which said anesthetic in liquid form is converted directly into said anesthetic gas, pressure control means for maintaining substantially constant the pressure of said anesthetic gas within said gasification chamber, and second delivery means for controllably delivering said anesthetic gas produced in said gasification chamber at said substantially constant pressure.

2. The apparatus of claim 1 wherein said pressure control means includes pressure maintenance means for maintaining substantially constant the pressure at which said anesthetic liquid is delivered to said gasification chamber.

3. The apparatus of claim 2 where said pressure maintenance means includes gas supply means for maintaining the pressure which is applied to said anesthetic liquid at a predetermined gas pressure level substantially corresponding to said pressure at which said anesthetic liquid is delivered to said gasification chamber.

4. The apparatus of claim 1 wherein said second delivery means includes control valve means for opening and closing said second delivery means whereby the frequency and period of said opening and closing of said control valve means can be controlled thereby.

5. The apparatus of claim 1 wherein said second delivery means includes a throttle valve.

6. The apparatus of claim 5 including throttle valve control means for controlling said throttle valve.

7. The apparatus of claim 1 wherein said gasification chamber is located above said reservoir means, and wherein said first delivery means comprises riser means extending into said reservoir means to a point below the level of said anesthetic liquid therein.

8. The apparatus of claim 7 wherein said gasification chamber includes a bottom wall portion, and wherein said riser means extends to said bottom wall portion of said gasification chamber.

9. The apparatus of claim 8 wherein said gasification chamber includes a top wall means, and wherein said delivery line means extends from said top wall means of said gasification chamber.

10. The apparatus of claim 1 further including condensation means associated with said second delivery means for converting said anesthetic gas back to its liquid state.

11. Apparatus for the production of predetermined dosages of a liquid comprising reservoir means for maintaining a supply of said liquid, gasification means comprising a gasification chamber, first delivery means for delivering said liquid from said reservoir means to said gasification chamber, temperature control means for maintaining said gasification chamber at a predetermined temperature at which said liquid is converted directly into gas form, pressure control means for maintaining the pressure of said gas within said gasification chambers substantially constant, second delivery means for controllably delivering said gas from said gasification chamber at said substantially constant pressure, and condensation means for converting the delivered gas back to its liquid state.

* * * * *